United States Patent [19]

Miyawaki

[11] Patent Number: 5,193,548
[45] Date of Patent: Mar. 16, 1993

[54] ELECTRONIC BLOOD PRESSURE METER

[75] Inventor: Yoshinori Miyawaki, Otsu, Japan

[73] Assignee: Omron Corporation, Kyoto, Japan

[21] Appl. No.: 610,208

[22] Filed: Nov. 8, 1990

[30] Foreign Application Priority Data

Nov. 8, 1989 [JP] Japan .................................. 1-290654

[51] Int. Cl.⁵ .............................................. A61B 5/022
[52] U.S. Cl. .................................... 128/680; 128/681;
128/682
[58] Field of Search ............... 128/680, 681, 682, 683,
128/670, 666

[56] References Cited

U.S. PATENT DOCUMENTS

| 4,105,021 | 8/1978 | Williams et al. ..................... 128/683 |
| 4,271,843 | 9/1981 | Flynn . | |
| 4,703,760 | 3/1987 | Miyawaki et al. . | |
| 4,712,563 | 12/1987 | Link . | |
| 4,844,084 | 7/1989 | Yamasawa ........................... 128/681 |
| 4,862,895 | 9/1989 | Yamasawa et al. ................. 128/680 |
| 4,872,461 | 10/1989 | Miyawaki . | |

FOREIGN PATENT DOCUMENTS 0207807 7/1987 European Pat. Off. .

Primary Examiner—Lee S. Cohen
Assistant Examiner—Brian L. Casler
Attorney, Agent, or Firm—Fish & Richardson

[57] ABSTRACT

An electronic blood pressure meter is disclosed which measures diastolic blood pressure. The blood pressure meter includes a cuff, a device for pressurizing and a device for depressurizing the cuff, and a device for detecting pressure in the cuff over time. A device is provided for detecting pulse waves, preferably in the form of an infrared light source and a reflected light detector. Processing circuitry is provided which detects either appearance or disappearance of a flat portion in the pulse wave by differentiating the pulse wave, measuring successive durations of time during which the differentiated pulse wave is between predetermined threshold values, and determining the moment at which the durations of time become less than a predetermined amount. The diastolic blood pressure value is then determined as the measured pressure in the cuff at the moment the flat portion of the pulse wave has appeared or disappeared.

4 Claims, 3 Drawing Sheets

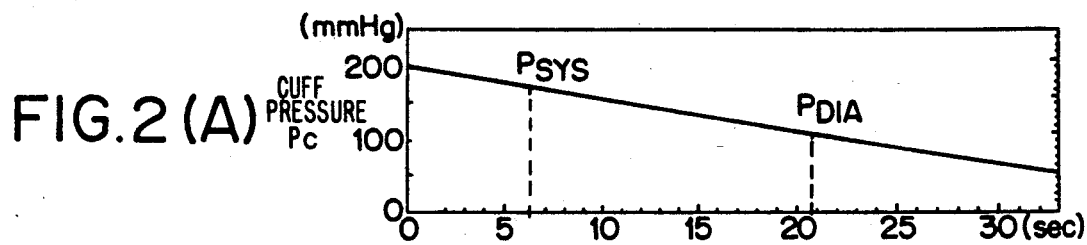
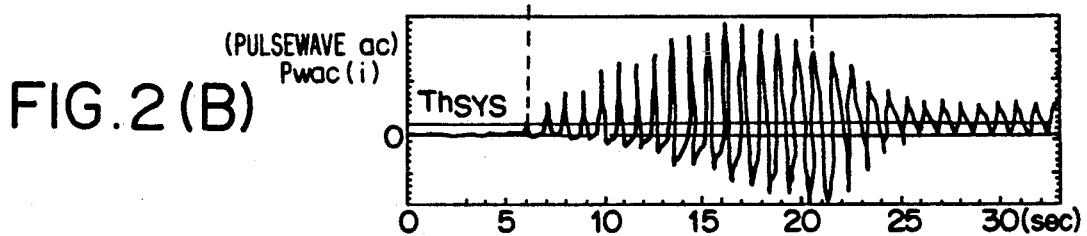
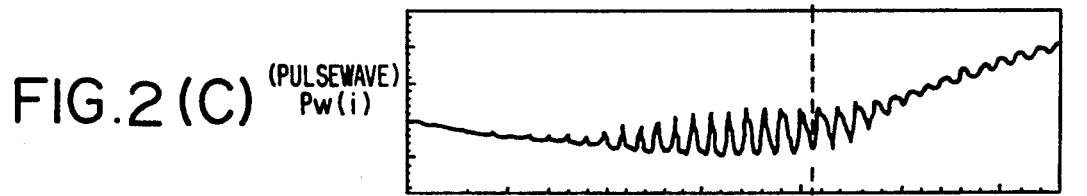
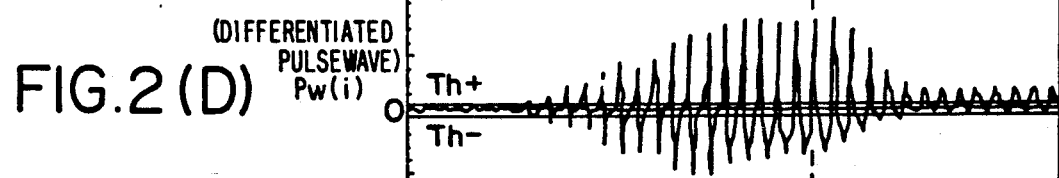
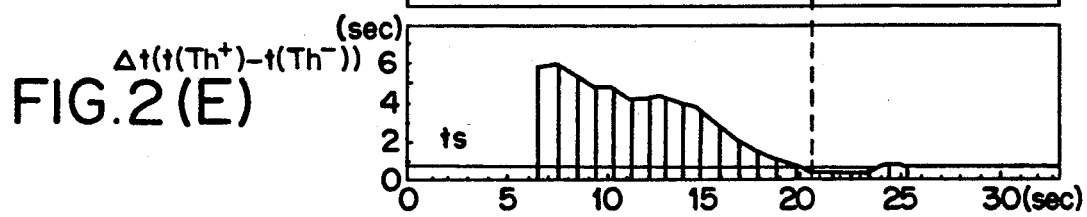

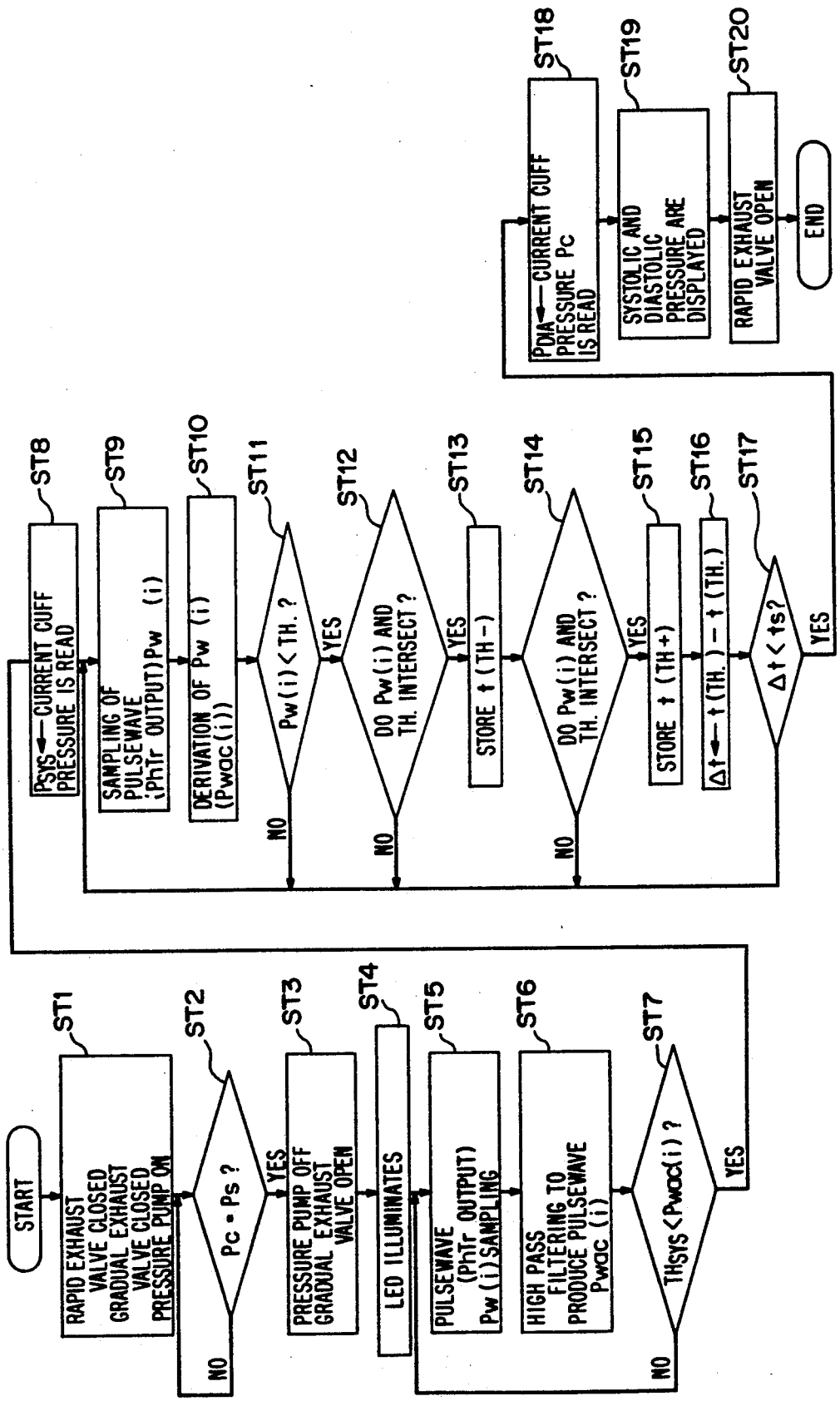

ELECTRONIC BLOOD PRESSURE METER

FIELD OF THE INVENTION

This invention relates to a blood pressure meter which can measure blood pressure values based on changes in the waveform of the pulse wave, and in particular, an electronic blood pressure meter which can measure diastolic blood pressure values.

BACKGROUND OF THE INVENTION

Conventionally, electronic blood pressure meters which determined blood pressure value based on changes in pulse waveform employed two methods to determine the diastolic pressure value. One method was to use the cuff pressure value at the moment the pulse wave was first detected as the systolic pressure and to consider the cuff pressure at the moment the maximum pulse wave was detected to be the average blood pressure. These values for systolic pressure and average pressure were then employed in a specified algorithm to calculate the diastolic pressure value. The other method was to use a value relative to the amplitude of the systolic pulse wave. When the pulse wave amplitude is decreasing, one can detect the point at which the pulse amplitude comes closest to the threshold value, which is a given ratio (approximately 70%) of the systolic pulse wave amplitude. The cuff pressure at this moment will be the diastolic pressure value.

In the first method of determining the diastolic pressure described above (calculating diastolic pressure value from systolic and average pressure values), it is assumed that the average pressure value is between the systolic and diastolic pressure values, and also that the value will lie ⅓ of the distance between the diastolic and systolic pressure values. However, blood pressure waveforms vary from person to person and according to the state of health of any given person, and there are many cases in which the average pressure will be quite different from that predicted by this formula. Thus there is a danger that the use of this method will produce large errors in diastolic pressure values depending on the conditions of measurement.

The second method described above for determining the diastolic pressure value (considering the diastolic pressure value to be the cuff pressure value at 70% of the systolic waveform amplitude when the amplitude is decreasing) is simply based on statistical experience and has only a weak theoretical basis. Poor reliability of measurement accuracy can also be problematic using this method.

SUMMARY OF THE INVENTION

In view of such problems in the prior art, an important feature of this invention is to furnish an electronic blood pressure meter which employs a method of determining diastolic pressure that can obviate the above problems. This device uses a method which is theoretically straightforward and which enjoys a high degree of precision and reliability.

The features of this invention can be accomplished by providing an electronic blood pressure meter which includes a cuff; a means to pressurize a liquid within the cuff; a means to depressurize the liquid within the cuff; a means to detect the pressure of the liquid within the cuff; a means, which can be integral with the cuff, to detect the pulse wave within the cuff; and a means to determine the blood pressure value based on the pressure of the liquid determined by the pressure detecting means and on the detected pulse wave.

This blood pressure meter has means to extract the flat portion of the detected pulse wave during the heart's diastolic phase. The pressure value within the cuff at the moment when this flat portion disappears, if measured during depressurization, or appears for the first time, if measured during pressurization, can be considered the diastolic pressure.

To determine the diastolic blood pressure value with an electronic blood pressure meter according to this invention, the flat portion is extracted from the waveform of the detected pulse wave. The cuff pressure value at the point when this flat portion vanishes (when measured during decrease of pressure) is considered the diastolic blood pressure. We found that when the cuff pressure is greater than the systolic pressure, the blood vessels become flattened (i.e., they are compressed). The volume of the compressed vessels remains unchanged, and this causes a segment of the pulse wave during diastole to remain unchanged (i.e., the flat period). If the cuff pressure is between the systolic and diastolic pressures, there will be some intervals when the blood pressure is lower than the cuff pressure. In those intervals, the vessels will be compressed and the pulse wave will become flat. If the cuff pressure is so low that it falls below the diastolic pressure, no parts of the vessels will be constricted, and the flat portion of the pulse wave will vanish. Thus the cuff pressure at the moment when the flat portion of the pulse wave vanishes can be considered the diastolic pressure. This method of determining the diastolic pressure is theoretically straightforward and offers highly reliable accuracy of measurement.

The concrete means used to measure the point at which the flat portion of the pulse wave vanishes is as follows. The waveform of the pulse wave is differentiated, and the time is detected when the differentiated pulse wave signal (the differentiated pulse wave) is in the vicinity of the zero level. This time is detected first by establishing specified threshold levels for the differentiated pulse wave (a level for the plus side and a level for the minus side). The time is then counted from the moment the differentiated pulse wave intersects the minus side level to the moment when it intersects the plus side level. When this detected time falls below the specified value, the flat portion of the pulse wave has vanished. The cuff pressure value at this moment can be considered the diastolic pressure.

With this invention, as described above, one can extract the flat portion of the pulse wave detected while the heart is in diastole. If measured during depressurization of the cuff, the cuff pressure at the point where this flat portion disappears corresponds to the diastolic pressure. If measured during pressurization, the cuff pressure at the point where it appears indicates the diastolic pressure. This method of determining the diastolic pressure is theoretically straightforward, and there is no danger of measurement errors due to variation among individuals or changes in state of health.

BRIEF DESCRIPTION OF THE DRAWINGS

FIG. 2(A) shows how the cuff is pressurized to a designated value and then depressurized in order to determine blood pressure values.

FIG. 2(B) shows the pulse waveform achieved by filtering the detected pulse waveform through a high pass filter, as well as the determination of the systolic pressure.

FIG. 2(C) shows the pulse waveform output by the phototransistor.

FIG. 2(D) shows the pulse waveform produced by performing a derivative operation on the pulse wave.

FIG. 2(E) shows the determination of the diastolic pressure.

FIG. 3 is a flowchart showing the flow of operations performed by the electronic blood pressure meter in the Example.

DETAILED DESCRIPTION OF THE INVENTION

Figure 1:
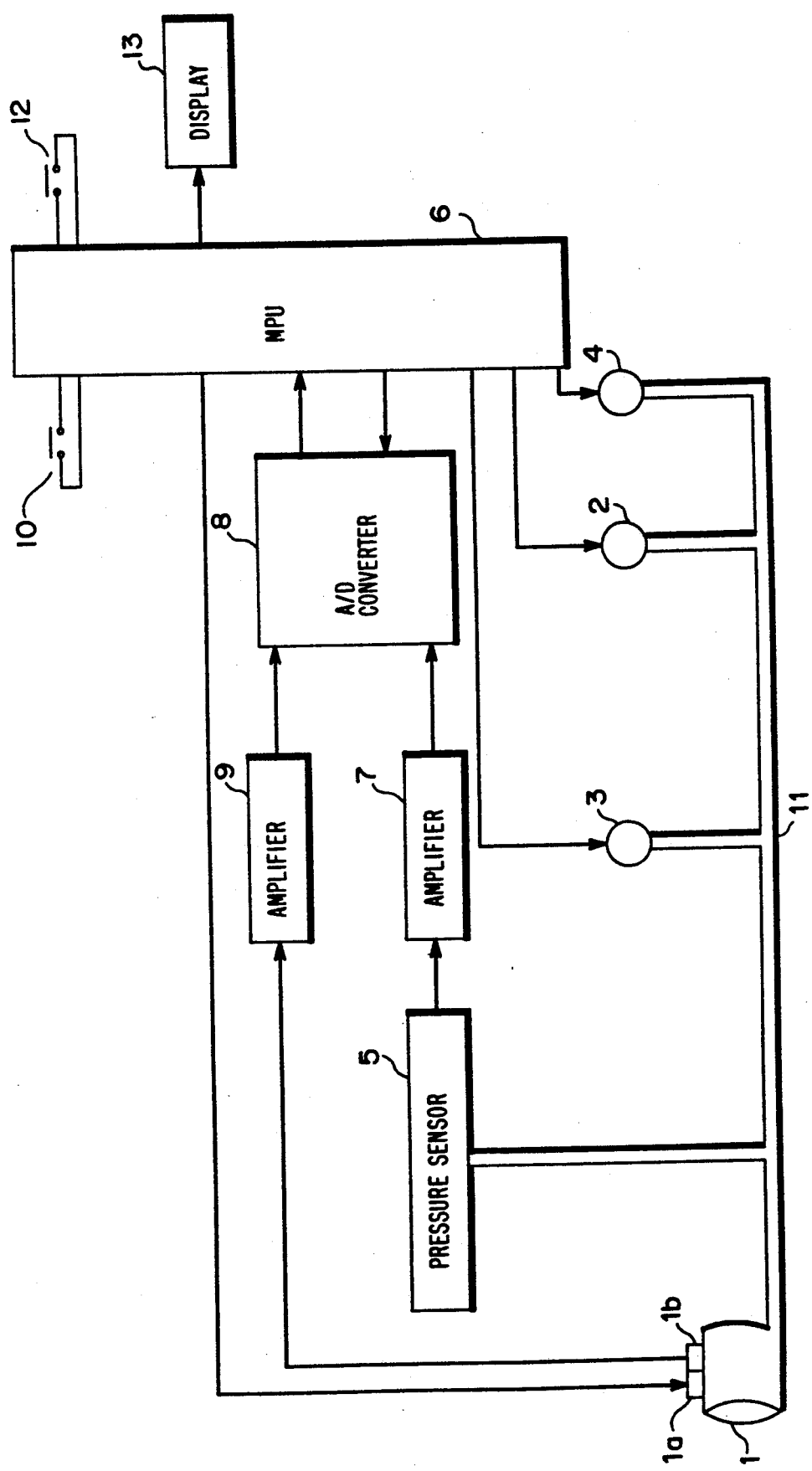
FIG. 1 is a block diagram of the electronic blood pressure meter disclosed in the Example below.

Finger cuff 11 in FIG. 1 is connected via tube 11 to pressure pump 2 (the means to pressurize the liquid); rapid exhaust valve 3; gradual exhaust valve 4; and pressure sensor 5 (the means to detect the pressure). Mounted to cuff 1 are infrared LED 1a and phototransistor 1b. For pressure sensor 5, one might use a diaphragm-type pressure transducer with a strain gauge, a semiconductor pressure transducer element, or some similar device. The above-described infrared LED 1a, pressure pump 2, and exhaust valves 3 and 4 are controlled by MPU (processing unit) 6, which will be described below. The output signal from pressure sensor 5 (an analog quantity) is amplified by amplifier 7 and converted to digital values by A/D converter 8. MPU 6 accepts the output signal from pressure sensor 5, now digitized, at fixed intervals. The abovementioned phototransistor 1b receives the reflection of the infrared light emitted by LED 1a onto the blood vessels within cuff 1. It then outputs the photoelectric signal (the pulse wave signal) to MPU 6 by way of amplifier 9 and A/D converter 8. The quantity of light received by phototransistor 1b varies as follows. If the cuff pressure exceeds the systolic blood pressure, the blood vessels will be compressed such that they contain no blood. When this happens, the infrared light will be amply reflected by the tissues below the skin of the finger, and a large quantity of light will be transmitted to phototransistor 1b. When the cuff pressure falls below the systolic blood pressure, the blood begins to flow again, and the infrared light is absorbed by the oxygenated hemoglobin in the blood in a ratio relative to the blood volume. Thus the quantity of light reflected back to phototransistor 1b decreases. The digitized signal for the quantity of infrared light (pulse wave signal Pw (i)) is transmitted to MPU 6.

In MPU 6, the detected pulse wave Pw (i) [See FIG. 2(C)] is filtered through a high pass filter which produces signal Pwac (i) [See FIG. 2(B)]. This signal exceeds a specified value $Th_{SYS}$ when the blood has begun to flow. The cuff pressure at this time can be considered the systolic pressure $P_{SYS}$. A derivative operation is performed on output signal Pw (i) from phototransistor 1b (pulse wave differentiation function). During the rise time of the differentiated pulse wave signal [See FIG. 2(D)], the amount of time that it is in the vicinity of "0" corresponds to the flat portion of the pulse wave is measured. This time ($\Delta t$) is the segment when Pw (i) is between the two previously defined threshold levels (negative side $Th_-$, positive side $Th_+$). When this time $\Delta t$ falls below a specified value $t_s$ [See Diagram 2 (E)], the flat portion of the pulse wave has disappeared. The cuff pressure at this time can be considered the diastolic blood pressure $P_{DIA}$.

FIG. 3 shows how the process works in the electronic blood pressure meter. The patient inserts his finger into cuff 1 and presses power switch 10 and start switch 12. Rapid exhaust valve 3 and gradual exhaust valve 4 close, and pressure pump 2 begins operating [Step (below, "ST") 1]. This causes cuff 1 to be pressurized to a designated value Ps which exceeds the systolic pressure, whereupon the flow of blood in the artery is obstructed. In ST 2, a judgment is made as to whether or not the cuff pressure Pc has attained the designated value Ps. If the cuff pressure Pc is equal to the designated value Ps, the judgment in ST 2 will be YES, pressure pump 2 will shut off, and gradual exhaust valve 4 will open (ST 3). Cuff 1 has entered its decompression stage (the measurement stage) [See FIG. 2(A)]. At this point, infrared LED 1a illuminates (ST 4) and emits infrared light to the blood vessels within cuff 1. Sampling is performed on pulse wave Pw (i) (ST 5). In other words, infrared light is emitted from LED 1a to the blood vessels and artery within cuff 1, and the reflected light enters phototransistor 1b.

Phototransistor 1b outputs a (pulse wave) signal corresponding to the quantity of light received, and this signal is transmitted to MPU 6 [See FIG. 2(C)]. This pulse wave signal Pw (i) is filtered through a high pass filter and transformed into pulse waveform Pwac (i), which is shown in FIG. 2(B) (ST 6).

In ST 7, a judgment is made as to whether or not pulse waveform Pwac (i) is greater than the reference value for the systolic pressure (the threshold value) $Th_{SYS}$. Cuff 1 is pressurized, the blood flow in the finger's arteries is obstructed, and the pressure is then allowed to decrease. At that point, the cuff pressure is high enough to exceed the systolic pressure, and the blood vessels are compressed (flattened). When there is no blood flow, no pulse wave is generated, and the pattern is flat. Thus pulse waveform Pwac (i) is below the designated value for $Th_{SYS}$, and the judgment in ST 7 is NO. However, if the cuff pressure drops by a certain amount, a small quantity of blood will begin to flow. In other words, pulse wave signal Pwac (i) will exceed the designated value $Th_{SYS}$. At this time the judgment in ST 7 will be YES. As blood flow has begun, the cuff pressure Pc is read, and this pressure is deemed to be the systolic pressure $P_{SYS}$ (ST 8).

Sampling is resumed on the output signal (pulse wave Pw (i)) from phototransistor 1b, and we proceed to the measurement of the diastolic pressure (ST 9). First, a derivative operation is performed on the pulse wave which was detected, Pw (i) (ST 10). This results in the pulse waveform shown in FIG. 2(D). ST 11 through 16, described below, comprise the detection of the flat portion of differentiated pulse wave Pw (i). When the cuff pressure is between the systolic and diastolic pressures, there will be some intervals when the blood pressure is lower than the cuff pressure. In these intervals, the vessels will be compressed, and the pulse wave will be flat. When the rising period of the differentiated pulse wave Pw (i) is in the vicinity of "0 level," this corresponds to the flat portion of the pulse wave. This time, during which the differentiated pulse wave Pw (i) is in the vicinity of "0 level," is measured. This time ($\Delta t$) indicates the segment when the differentiated pulse wave Pw (i) is between the two previously specified threshold levels (negative side $Th_-$ and positive side $Th_+$). We ascertain this time by measuring it.

In ST 11, a judgment is made as to whether or not the differentiated pulse wave Pw (i) is smaller than $Th_-$ (the threshold level specified for the minus side of zero). If the differentiated pulse wave Pw (i) is smaller than the negative threshold $Th_-$, or in other words if the pulse wave has crossed the negative threshold level, the judgment in ST 11 will be YES.

In ST 12, a judgment is made as to whether or not the differentiated pulse wave Pw (i) and the negative threshold level intersect each other. If differentiated pulse wave Pw (i) has also crossed the negative threshold level, the judgment in ST 12 will be YES. The time at which this occurred will be stored (ST 13) as $t(Th_-)$, the moment of intersection of Pw (i) and $Th_-$. In ST 14 a judgment is made as to whether or not differentiated pulse wave Pw (i) and positive threshold $Th_+$ intersect each other. If differentiated pulse wave Pw (i) has also crossed the positive threshold level, the judgment in ST 14 will be YES, and this time will be stored (ST 15) as $t(Th_+)$, the moment of intersection of Pw (i) and $Th_+$. The time during which the differentiated pulse wave is in the vicinity of "0 level" (the time that the flat portion of the pulse wave occurs) will determine $\Delta t$. This time is arrived at by the formula $t(Th_+) - t(Th_-)$. (ST 16)

In ST 17, a judgment is made as to whether or not the time $\Delta t$ that the differentiated pulse wave Pw (i) is flat is less than the specified value $t_s$ which is shown in Diagram 2 (E). If $\Delta t$ is below the previously specified value $t_s$, then we can conclude that the flat portion of the pulse wave has vanished. For example, if the measured time $\Delta t$ is below the specified value $t_s$, the judgment in ST 17 will be YES, and the cuff pressure Pc will be read at this moment (ST 18). This cuff pressure Pc is considered to be the diastolic pressure $P_{DIA}$. The systolic pressure $P_{SYS}$ and the diastolic pressure $P_{DIA}$, which are shown in FIG. 2(A), are displayed by display 13 (ST 19). Rapid exhaust valve 3 opens, and the measurement is completed.

Cuff 1 was pressurized until its pressure exceeded the systolic pressure, and the diastolic pressure was determined while the cuff was undergoing depressurization (measurement during depressurization). For this reason, the diastolic pressure was determined by finding the point where the flat portion of the pulse wave vanishes. To determine diastolic pressure while the cuff is being pressurized, one can find the point where the flat portion of the pulse wave first appears.

I claim:

1. A blood pressure monitor, comprising:
   a cuff;
   pressurization means for pressurizing the cuff;
   depressurization means for depressurizing the cuff;
   pressure detection means for detecting pressure in the cuff over time and producing an output indicative of the pressure in the cuff;
   pulse wave detection means for detecting pulse waves and for producing pulse wave data during the depressurization of the cuff;
   flat portion detection means for detecting from the pulse wave data presence or disappearance of a flat portion in the pulse wave, wherein said flat portion detection means comprises:
      differentiating means for differentiating the pulse wave data to produce a differentiated pulse wave, time measurement means for measuring successive durations of time during which the differentiated pulse wave is between predetermined threshold values, and
      flat portion disappearance detecting means for detecting a moment of disappearance of the flat portion by determining a moment at which said successive durations of time become less than a predetermined amount; and
   diastolic blood pressure value determining means for determining a diastolic blood pressure value by obtaining the output of the pressure detection means at the moment of disappearance of the flat portion in the pulse wave.

2. A blood pressure monitor, comprising:
   a cuff;
   pressurization means for pressurizing the cuff;
   depressurization means for depressurizing the cuff;
   pressure detection means for detecting pressure in the cuff over time and producing an output indicative of the pressure in the cuff;
   pulse wave detection means for detecting pulse waves and for producing pulse wave data during the pressurization of the cuff;
   flat portion detection means for detecting from the pulse wave data presence or appearance of a flat portion in the pulse wave, wherein said flat portion detecting means comprises:
      differentiating means for differentiating the pulse wave data to produce a differentiated pulse wave,
      time measurement means for measuring successive durations of time during which the differentiated pulse wave is between predetermined threshold values, and
      flat portion appearance detecting means for detecting a moment of appearance of the flat portion by determining a moment at which said successive durations of time become less than a predetermined amount; and
   diastolic blood pressure value determining means for determining a diastolic blood pressure value by obtaining the output of the pressure detection means at the moment of appearance of the flat portion in the pulse wave.

3. A method for determining diastolic blood pressure value while a cuff is being depressurized, comprising the steps of:
   pressurizing the cuff to a value which exceeds a diastolic pressure value;
   directing light onto blood vessels within the cuff while depressurizing the cuff;
   receiving light reflected off the blood vessels within the cuff and sampling a pulse wave from the received reflected light to produce pulse wave data;
   determining a moment at which a flat portion of the pulse wave disappears by differentiating the pulse wave data to produce a differentiated pulse wave, measuring successive durations of time during which the differentiated pulse wave is between predetermined threshold values, and determining a moment at which said successive durations of time become less than a predetermined amount; and
   detecting a cuff pressure value at the moment at which the flat portion of the pulse wave disappears.

4. A method for determining diastolic blood pressure value while a cuff is being pressurized, comprising the steps of:
   directing light onto blood vessels within the cuff while pressurizing the cuff to a value which exceeds a diastolic pressure value;

receiving light reflected off the blood vessels within the cuff and sampling a pulse wave from the received reflected light to produce pulse wave data;

determining a moment at which a flat portion of the pulse wave disappears by differentiating the pulse wave data to produce a differentiated pulse wave, measuring successive durations of time during which the differentiated pulse wave is between predetermined threshold values, and determining a moment at which said successive durations of time become less than a predetermined amount; and detecting a cuff pressure value at the moment at which the flat portion of the pulse wave appears.

* * * * *